United States Patent [19]

Mundy et al.

[11] Patent Number: 5,599,708
[45] Date of Patent: Feb. 4, 1997

[54] OSTEOCLAST GROWTH REGULATING FACTORS AND ANTIBODIES

[75] Inventors: Gregory R. Mundy, San Antonio, Tex.; Wilson H. Burgess, Gaithersburg, Md.; Toshiyuka Yoneda, San Antionio, Tex.

[73] Assignee: Osteosa Liquidation Trust, San Antonio, Tex.

[21] Appl. No.: 279,675

[22] Filed: Jul. 25, 1994

Related U.S. Application Data

[63] Continuation of Ser. No. 59,722, May 10, 1993, abandoned, which is a continuation of Ser. No. 733,420, Jul. 23, 1991, abandoned.

[51] Int. Cl.$^6$ .................. C12N 15/13; A61K 39/395; C07K 14/00; C12P 21/02
[52] U.S. Cl. .................. 435/240.27; 424/138.1; 424/145.1; 424/155.1; 424/174.1; 424/178.1; 424/185.1; 424/198.1; 435/70.2; 435/172.2; 530/326; 530/388.24; 530/389.1; 530/413
[58] Field of Search ............ 424/138.1, 145.1, 424/155.1, 158.1, 174.1, 178.1, 185.1, 198.1; 435/240.3, 172.2, 70.2, 740.27; 530/326, 387.7–387.9, 388.24, 413, 391.3, 389.1

[56] References Cited

U.S. PATENT DOCUMENTS 5,169,837 12/1992 Lagarde et al. .................. 514/21

OTHER PUBLICATIONS

Rudinger *Pepticle Harmones* ed Parsons Univ. Park Press 1976 pp. 1–7.

Yoneda et al Oral Surg Oral Med Oral Pathology 68:604–611 1989.

Mundy Trends Endo. Metab. 1:307–311 1990.

Yoneda J. Clin. Oncol 9:468–477 1991.

Josse, et al J. Clin Invest G7:1472–1481 1981.

Waldmann Science 252:1657–1662 1991.

Current Protocols in Molecular Biology 1987 Wiley & Sones Chapters 10 & 11.

Yoneda et al Cancer Research 51:2438–2443 1991.

*Primary Examiner*—Robert D. Budens
*Assistant Examiner*—Julie E. Reeves
*Attorney, Agent, or Firm*—Arnold White & Durkee

[57] ABSTRACT

The present invention relates to a novel osteoclast growth regulatory factor, hereinafter referred to as "osteoclastpoietic factor (OPF)," which stimulates the formation of osteoclast bone cells, a process of preparing same, therapeutic and diagnostic uses thereof, antibodies to and antagonists of OPF, and assays for OPF, all of which relate to the development of therapeutics for the prevention and treatment of diseases involving bone tissue, for example, osteoporosis, Paget's disease and osteopetrosis.

18 Claims, 6 Drawing Sheets

C_8 Analytical Reverse-phased HPLC of G-50 Peak

Effect of Synthetic OPF on Bone Resorption

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
    ( A ) LENGTH: 16 amino acids
    ( B ) TYPE: amino acid
    ( D ) TOPOLOGY: linear ( i i ) MOLECULE TYPE: peptide ( x i ) SEQUENCE DESCRIPTION: SEQ ID NO:1:

Ala Val Gln Arg Tyr Leu Val Leu Gln Gly Val Ser Pro Ala Gln Leu
  1               5                   10                  15

( 2 ) INFORMATION FOR SEQ ID NO:2:

( i ) SEQUENCE CHARACTERISTICS:
    ( A ) LENGTH: 17 amino acids
    ( B ) TYPE: amino acid
    ( D ) TOPOLOGY: linear ( i i ) MOLECULE TYPE: peptide ( x i ) SEQUENCE DESCRIPTION: SEQ ID NO:2:

Lys Ala Val Gln Arg Tyr Leu Val Leu Gln Gly Val Ser Pro Ala Gln
  1               5                   10                  15
  Leu ( 2 ) INFORMATION FOR SEQ ID NO:3:

( i ) SEQUENCE CHARACTERISTICS:
    ( A ) LENGTH: 51 base pairs
    ( B ) TYPE: nucleic acid
    ( C ) STRANDEDNESS: double
    ( D ) TOPOLOGY: linear ( i i ) MOLECULE TYPE: other nucleic acid ( x i ) SEQUENCE DESCRIPTION: SEQ ID NO:3:

AARGCNGTNC ARMGNTAYYT NGTNYTNCAR GGNGTNWSNC CNGCNCARYT N        51

OSTEOCLAST GROWTH REGULATING FACTORS AND ANTIBODIES

This is a continuation of U.S. patent application Ser. No. 08/059,722 filed on 10 May 1993, now abandoned, which is a continuation of U.S. patent application Ser. No. 07/733,420 filed on 23 Jul. 1991, now abandoned.

FIELD OF THE INVENTION

The present invention relates to a novel osteoclast growth regulatory factor, hereinafter referred to as "osteoclastpoietic factor (OPF)," which stimulates the formation of osteoclast bone cells, a process of preparing same, therapeutic and diagnostic uses thereof, antibodies to and antagonists of OPF, and assays for OPF, all of which relate to the development of therapeutics for the prevention and treatment of diseases involving bone tissue, for example, osteoporosis, Paget's disease and osteopetrosis.

Living bone tissue is continuously being replenished by the process of resorption and deposition of calcium minerals. This process, described as, the absorption-resorption cycle, is facilitated by means of substantially two cell types, the osteoblasts and the osteoclasts. The osteoclast is a multinucleated cell and is the only cell in the body known to have the capacity to degrade (or resorb) bone. This resorption activity is accomplished by the osteoclast forming pits (resorption lacunae) in bone tissue, and, in fact, osteoclast activity in cell culture is measured by their capacity to form these pits on slices of mineralized tissue such as bone or sperm whale dentine. The osteoclast is derived from a hematopoietic precursor which it shares with the formed elements of the blood (Mundy & Roodman (1987) Osteoclast ontogeny and function. *In Bone and Mineral Research V:* 209–280. (ed. Peck) Elsevier). The precursor for the osteoclast is a mononuclear cell (cell with a single nucleus) which is found in the bone marrow and which forms the mature and unique multinucleated osteoclast after undergoing replication and differentiation by means of cell fusion. The mature osteoclast is distinguished from other multinucleated cells by the presence of the enzyme tartrate-resistant acid phosphatase (TRAP) which is often used as an osteoclast cell marker.

Cells found in blood and bone respond to specific protein factors excreted by other cells in response to various stimuli. These factors are referred to as cytokines, many of which have been identified by their biological characteristics and their unique amino acid sequences. Each cytokine presents a unique spectrum of characteristics utilized to distinguish each specific cytokine from others. Certain cytokines stimulate the growth and/or differentiation of specific types of cells, while other cytokines target cancerous cells for destruction. Exemplary cytokines include granulocyte-colony-stimulating factor (CSF), granulocyte-macrophage CSF, macrophage CSF, interleukin-1 beta, interleukin-3, interleukin-6, interferon-gamma, tumor necrosis factor, lymphotoxin, leukemia inhibitory factor, and transforming growth factor-alpha.

Among the pathological conditions associated with an abnormal osteoclast development or function are conditions wherein increased bone resorption results in the development of fragile and/or brittle bone structure, such as osteoporosis, or increased bone absorption results in the development of excess bone mass, such as osteopetrosis. It is believed that the development of excess or deficient populations of osteoclasts or osteoblasts results from a corresponding lack or excess of specific cytokines in the blood.

Many of the known cytokines stimulate or inhibit blood cells: Several growth regulatory cytokines such as CSF-M, transforming growth factor alpha, interleukin-1 and tumor necrosis factor have been shown to stimulate marrow mononuclear cell proliferation. Although cytokines such as interleukin-1 (IL-1), tumor necrosis factor (TNF) and interleukin-6 (IL-6) may influence osteoclast formation and differentiation (Mundy (1990) Trends Endo. Metab. 1:307–311), these factors are not specific osteoclast growth regulatory factors.

REPORTED DEVELOPMENTS

Recently, Yoneda et al isolated a human squamous cell tumor associated with leukocytosis and splenomegaly, hypercalcemia and increased osteoclastic bone resorption (Yoneda et al, (1989) Oral Surgery, Oral Medicine and Oral Pathology 68:604–611). Furthermore, when these tumors were surgically removed, there was a dramatic decrease in osteoclastic bone resorption and leukocyte count. Nude mice bearing the tumor also exhibited leukocytosis, splenomegaly, hypercalcemia and increased osteoclastic bone resorption. (Yoneda et al, 1991) *J. Clin. Oncol.* 9: 468–477).

The present invention relates to the isolation from the squamous tumor cells and characterization of a polypeptide having biological activity including regulatory activity associated with the development of multinucleated bone cells.

SUMMARY OF THE INVENTION

The present invention relates to a biologically active polypeptide comprising the amino acid sequence -A-V-Q-R-Y-V-L-Q-G-V-S-P-A-Q-L (SEQ ID NO: 1) or a biologically active sequence analogue thereof. Among the biological properties of the polypeptide of the present invention is the capability to regulate the growth and/or differentiation of osteoclast cells.

In another embodiment, the invention provides monoclonal and polyclonal antibodies capable of specifically binding to the amino acid sequence A-V-Q-R-Y-L-V-L-Q-G-V-S-P-A-Q-L (SEQ ID NO: 1) or a biologically active sequence analogue thereof, as well as uses of these monoclonal and polyclonal antibodies therapeutically and diagnostically. The antibodies of the present invention are useful for affinity purifying the naturally occurring polypeptide as well as active fragments thereof, in assays for detecting the present polypeptide and for treating pathological conditions resulting from over production thereof. The assays provide a method for the clinical diagnosis and assessment of those diseases in which there is excess production of the naturally occurring polypeptide, and for monitoring treatment efficacy.

The invention also provides compositions, such as diagnostic and pharmaceutical compositions, containing the polypeptide of the present invention and methods of using these in treatment and diagnosis.

In another embodiment, the present invention provides a method for the treatment of bone diseases characterized by abnormal osteoclast activity such as osteopetrosis, comprising administration of the present polypeptide to individuals in need of such treatment. Antagonists, such as the present antibodies to the present polypeptides, are useful for inhibiting bone resorption in a number of disease states where bone resorption is enhanced such as, but not limited to, osteoporosis, Paget's disease, malignant diseases which affect the skeleton such as myeloma and breast cancer, and chronic inflammatory diseases which cause localized bone loss such as rheumatoid arthritis and periodontal disease. Treatment of these diseases may be accomplished by administration of antagonists such as neutralizing antibodies to this and related polypeptides to individuals in need of such treatment.

Other and further objects features and advantages will be apparent from the following description of the presently preferred embodiments of the invention, given for the purposes of disclosure when taken in conjunction with the accompanying drawings.

BRIEF DESCRIPTION OF THE FIGURES

The invention will be more readily understood from a reading of the following specification and by reference to the accompanying drawings forming a part thereof.

DETAILED DESCRIPTION

Figure 1:
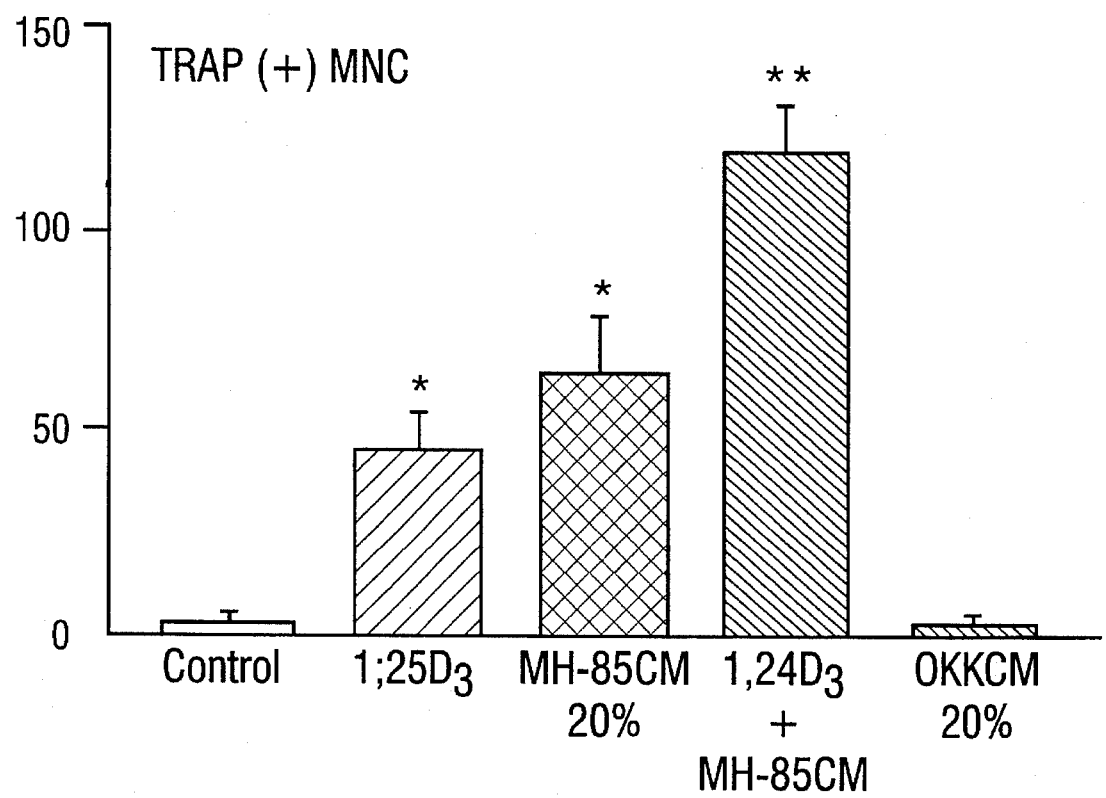
FIG. 1 demonstrates the effect of MH-85CM on TRAP(+)MNC formation in mouse bone marrow cultures.
Figure 2A:
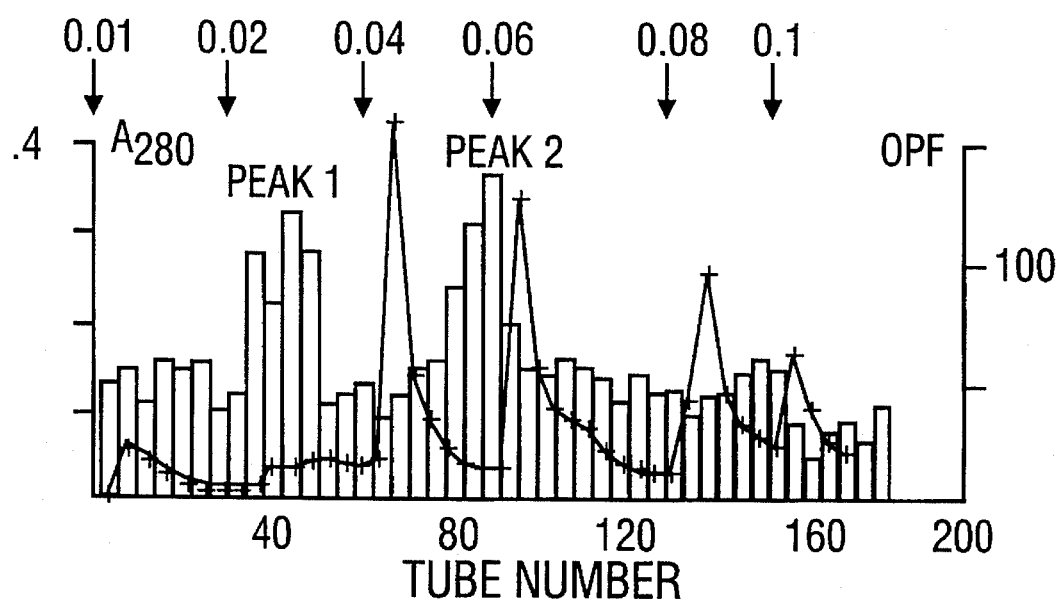
FIGS. 2A–2D demonstrate the profile of DEAE-Cellulose anion exchange column chromatography, of OPE (FIG. 2A), 6M–68F (FIG. 2B), 6C8F (FIG. 2C), and M-C8F (FIG. 2D).
Figure 2B:
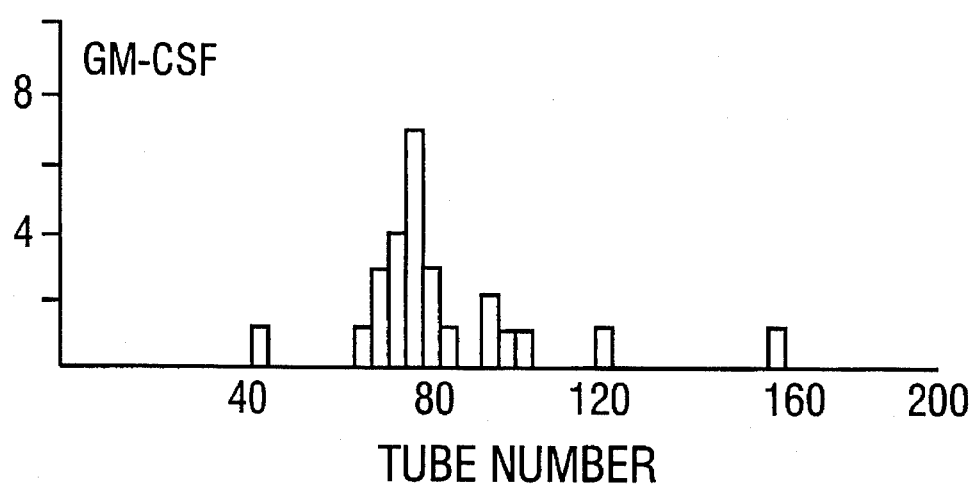
Figure 2C:
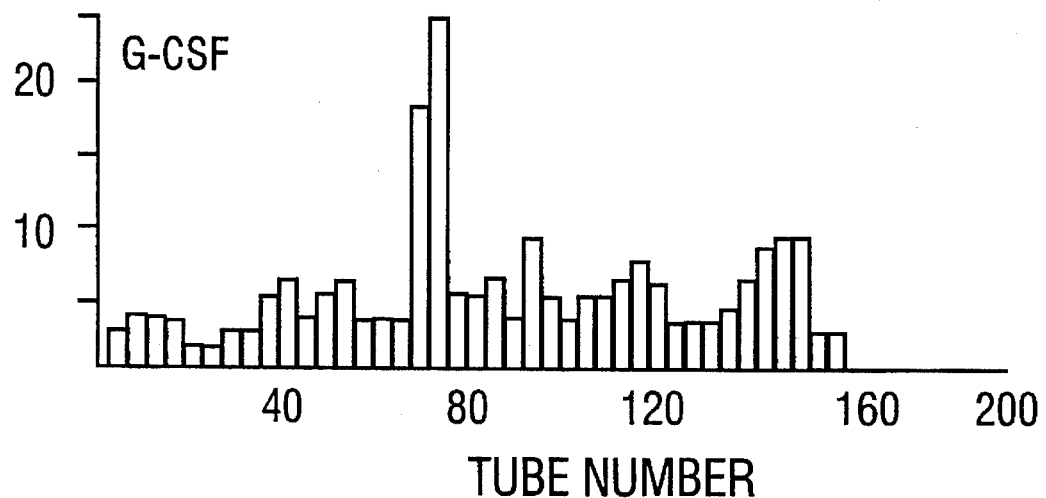
Figure 2D:
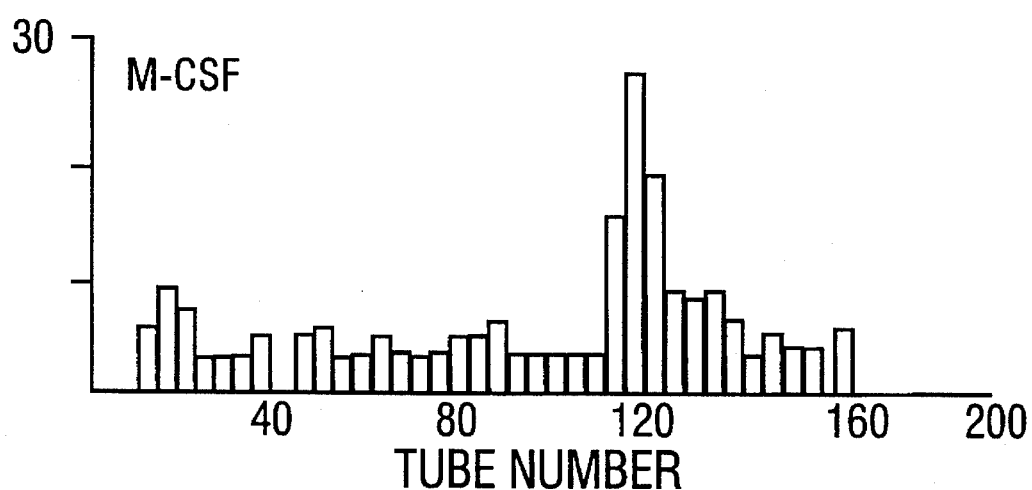

The present invention provides a biologically active polypeptide comprising the amino acid sequence -A-V-Q-R-Y-L-V-L-Q-G-V-S-P-A-Q-L (SEQ ID NO: 1) or a biologically active sequence analogue thereof. Among the biological properties of the polypeptide of the present invention is the capability to regulate the growth and/or differentiation of osteoclast cells.

Initially, a polypeptide capable of regulating the growth and/or differentiation of multinucleated osteoclast cells was isolated from a human squamous cell tumor. This polypeptide, referred to hereinafter as osteoclastpoietic factor, or OPF, has been isolated and substantially purified from conditioned medium from a cell line, MH-85, deposited under ATCC Number CRL 10833, established from the human tumor described by Yoneda et al. which was associated in the human host and in the nude mouse host with leukocytosis, splenomegaly, hypercalcemia and increased osteoclastic bone resorption. (Yoneda et al, 1991) *J. Clin. Oncol.* 9: 468–477). The present invention also provides an assay to detect the polypeptide of the present invention. Utilizing a synthetic (17-mer) polypeptide as a standard in an ELISA assay, OPF activity can also be detected in the conditioned media from other animal and human cultured tumor cells, stromal cell cultures, and media bathing murine splenic leukocytes stimulated with the mitogen concanavalin A. (Table 1) The limits of detection in the assay was 50 pg/ml.

TABLE 1

Detection of OPF from various sources.

| Cells | Source | Presence of OPF |
|---|---|---|
| MH-85 | human squamous carcinoma | + |
| RWGT2 | human squamous carcinoma | − |
| A375 | human melanoma | − |
| ST2 | murine stromal cells | + |
| 7M1 | murine stromal cells | + |
| 14M1 | murine stromal cells | + |
| MG63 | human osteosarcoma cells | − |
| SaOS | human osteosarcoma cells | − |
| ROS 17/2.8 | rat osteosarcoma cells | − |
| UMR-106 | rat osteosarcoma cells | − |
| MC3T3 | murine calvarial bone cells | − |
| Con A stimulated leukocytes | normal mouse spleen | + |

OPF was extensively purified and isolated in a substantially homogeneous form. OPF has a molecular weight of approximately 4000 daltons as assessed by gel filtration chromatography. At earlier stages of purification, the molecule having OPF activity is retained by filtration membranes which allow molecules less than 10,000 daltons to pass. The apparent higher molecular weight of the impure OPF might be due to aggregation of the active moiety in these less pure preparations or to association of the OPF molecule with another molecule.

The present invention also provides processes for purifying OPF. In one embodiment, the present invention provides a method for purifying OPF which comprises: collecting conditioned medium containing OPF from cultured cells; chromatographing said medium on anion exchange medium such as, but not limited to, DEAE-Cellulose; collecting the fractions containing the OPF activity and subjecting the pooled fractions to gel filtration chromatography on a Sephadex-G50 column; collecting the fractions containing OPF activity and further subjecting the pooled material to high pressure liquid chromatography; and recovering said OPF in substantially pure form. Chromatographic procedures may be carded out, preferably, in a narrow bore column containing a fine particle resin under increased pressure to enhance the effectiveness of separation, i.e., by high pressure liquid chromatography.

Concentration and salt removal are commonly used precursors to certain chromatographic or separation techniques employed in the invention. Salt removal may be performed by, for example, dialysis, gel filtration or control pore glass (CPG) chromatography. These preparation methods and the extent to which they are required for particular separation procedures are well known in the art.

In another embodiment, the present invention provides a method for purifying OPF comprising contacting a medium containing OPF mixed with other proteins with an antibody which binds to at least one epitope of the OPF molecule, removing the antibody-OPF complex, releasing the OPF from the antibody and separating the OPF from the antibody. In a preferred embodiment the antibody is bound to a solid support. The choice of solid support and methods for binding the antibody to the solid support are well known to those skilled in the art.

The amino acid sequence of a biologically active polypeptide which stimulates osteoclast development has been determined. The amino acid sequence which confers the biologic activity involved in regulating the enhancement of multinucleated osteoclast cells comprises -K-A-V-Q-R-Y-L-V-L-Q-G-V-S-P-A-Q-L (SEQ ID NO: 2). The present invention also provides a synthetic biologically active analogue having the biological activity of the naturally occurring OPF. The sequence of this synthetic 17-mer peptide is K-A-V-Q-R-Y-L-V-L-Q-G-V-S-P-A-Q-L (SEQ ID NO: 2). The amino acid sequence of the polypeptide of the present invention is distinct from the sequences of other proteins which have been shown to promote osteoclast formation.

The present invention provides a biologically active polypeptide comprising the amino acid sequence K-A-V-Q-R-Y-L-V-L-Q-G-V-S-P-A-Q-L (SEQ ID NO: 2) in substantially homogeneous form. The term "substantially homogeneous" when applied to the polypeptides of the present invention means that the polypeptide is essentially free of other proteins normally associated with OPF in its natural state. The term "substantially homogeneous" is not meant to exclude artificial or synthetic mixtures of OPF or other polypeptides of the present invention with other compounds.

The term "biologically active polypeptide" means naturally occurring OPF per se, as well as biologically active analogues thereof, synthetic produced polypeptides, natural and pharmaceutically acceptable salts and pharmaceutically acceptable derivatives. The term "OPF" also encompasses biologically active fragments thereof, as well as biologically active sequence analogues thereof. Different alleles of OPF may exist in nature. These variations may be characterized by differences in the nucleotide sequence of the structural gene coding for proteins of identical biological function. The term "biologically active sequence analogue" includes analogues having single or multiple amino acid substitutions, deletions, additions, or replacements. All such alleic variations, modifications, and analogues resulting in derivatives of OPF which retain one or more of the biologically active properties of native OPF are included within the scope of this invention.

The present invention also provides a nucleotide sequence encoding the biologically active polypeptides of the present invention. The DNA sequence (SEQ ID NO: 3) which encodes a polypeptide (SEQ ID NO: 2) of the present invention capable of regulating osteoclast cell differentiation is:

```
             5                    10                  15
K-  A-  V-  Q-  R-  Y-  L-  V-  L-  Q-  G-  V-  S-  P-  A-
AAR GCN GTN CAR CGN TAY CTN GTN CTN CAR GGN GTN TCN CCN GCN
            AGH     TTR     TTR             AGY

Q-  L
CAR CTN
    TTR
``` wherein Y is selected from T or C, R is selected from A or G and N is selected from G, A, T or C and G, A, T and C represent guanine, adenine, thymidine, and cytosine.

The biologically active polypeptides of the present invention may also be prepared utilizing recombinant technology. A recombinant DNA molecule coding for any of the polypeptides of the present invention can be used to transform a host using any of the techniques commonly known to those of ordinary skill in the art.

A gene is a DNA sequence which encodes through its copy or messenger RNA a sequence of amino acids characteristic of a specific peptide. The term cDNA includes genes from which the intervening sequences have been removed.

Methods for preparing fused, operably linked genes and expressing them in bacteria are known and are shown, for example, in U.S. Pat. No. 4,366,246, herein incorporated by reference. The genetic constructs and methods described therein can be utilized for expression of the polypeptides of the present invention in prokaryotic or eukaryotic hosts. Hosts transformed with the polypeptides of the present invention are particularly useful for the production of polypeptides of the present invention The invention extends to any host modified according to the methods described, or modified by any other methods, commonly known to those of ordinary skill in the art, such as, for example, by transfer of genetic material using an expression plasmid lysogenic phage, and which yields a prokaryote or eukaryote expressing the gene for OPF.

Especially preferred is the use of a vector containing coding sequence for the polypeptides of the present invention for purposes of prokaryote transformation.

The term "host" as used herein is meant to include not only prokaryotes but also eukaryotes such as yeast as well as plant and animal cells. The term "prokaryote" is meant to include all bacteria which can be transformed with the DNA for the expression of the polypeptides of the present invention. Prokaryotic hosts may include Gram negative as well as Gram positive bacteria, such as *E. coli, S. tymphimurium, Serratia marcescens,* and *Bacillus subtilis*. In addition to prokaryotes, eukaryotic microbes, such as yeast cultures, may also be used. The term "eukaryote" is meant to include all yeasts, fungi, animal and plant cells which can be transformed with the DNA for the expression of the polypeptides of the present invention. Eukaryotic hosts may include yeasts such as *Pichia pastoris* or mammalian cells. *Saccharomyces cerevisiae*, or common baker's yeast, is the most commonly used among eukaryotic microorganisms, although a number of other strains are commonly available. Yeast promoters suitable for the expression of foreign DNA sequences in yeast include the promoters for 3-phosphoglycerate kinase or other glycolytic enzymes. Suitable expression vectors may contain termination signals which provide for the polyadenylation and termination of the mRNA transcript of the cloned gene. Any vector containing a yeast-compatible promoter, origin of replication, and appropriate termination sequence is suitable for expression of the polypeptides of the present invention.

A cloning vehicle is a plasmid or phage DNA or other DNA sequence which is able to replicate in a host cell which is characterized by one or a small number of endonuclease recognition sites at which such DNA sequences may be cut in a determinable fashion without loss of an essential biological function of the DNA, and which contains a marker suitable for use in the identification of transformed cells. Markers, for example, are tetracycline resistance, neomycin resistance or ampicillin resistance. The word "vector" is sometimes used for cloning vehicle.

An expression vehicle is a vehicle similar to a cloning vehicle but which is capable of expressing a given structural gene in a host, normally under control of certain control sequences. "Expression vectors" refer to vectors which are capable of transcribing a DNA sequences contained therein, where such sequences are linked to other regulatory sequences capable of affecting their expression.

The expression vector typically contains an origin of replication, promoter(s), terminator(s), a ribosome binding site, as well as specific genes which are capable of providing phenotypic selection in transformed cells. These expression vectors must be replicable in the host organisms or systems either as episomes, bacteriophage, or as an integral part of the chromosomal DNA. The transformed hosts can be fermented and cultured according to means known in the art to achieve optimal cell growth.

Examples of promoters which can be used in the invention include, but are not limited to: rec A, trp, lac, tac, bacteriophage lambda pR or pL, MMTV, SV40. Examples of some of the plasmids or bacteriophage which can be used in the invention are listed in Maniatis et al., *Molecular Cloning*, Cold Spring Harbor Laboratories, 1982, and others are known to those of skill in the art and can be easily ascertained.

Recombinant vectors and methodology disclosed herein are suitable for use in host cells covering a wide range of prokaryotic and eukaryotic organisms. Prokaryotic cells are preferred for the cloning of DNA sequences and in the construction of vectors. For example, *E. coli* K12 strain HB101 (ATCC no. 33694), is particularly useful. Of course, other microbial strains may be used.

Cell lines derived from multicellular organisms may also be used as hosts. In principle, any such cell culture is workable, whether from a vertebrate or invertebrate source. However, interest has been greatest in vertebrate cells, and propagation of vertebrate cells in culture (tissue culture) has become a routine procedure in recent years. Examples of such useful hosts are the VERO, HeLa, mouse C127, Chinese hamster ovary (CHO), WI38, BHK, COS-7, and MDCK cell lines. Expression vectors for such cells ordinarily include an origin of replication, a promoter located in front of the gene to be expressed, RNA splice sites (if necessary), and transcriptional termination sequences.

For use in mammalian cells, the control functions (promoters and enhancers) on the expression vectors are often provided by viral material. For example, commonly used promoters are derived from polyoma, Adenovirus 2, and most frequently, Simian Virus 40 (SV40). Eukaryotic promoters, such as the promoter of the murine metallothionein gene [Paulakis and Hamer, *Proc. Natl. Acad. Sci.* 80:397–401 (1983)], may also be used. Further, it is also possible, and often desirable, to utilize the promoter or control sequences which are naturally associated with desired gene sequence, provided such control sequences are compatible with the host system. To increase the rate of transcription, eukaryotic enhancer sequences can be obtained from a variety of animal cells or oncogenic retroviruses such as the mouse sarcoma virus.

An origin of replication may be provided either by construction of the vector to include an exogenous origin, such as that provided by SV40 or other viral sources, or may be provided by the host cell chromosomal replication mechanism. If the vector is integrated into the host cell chromosome, the latter is often sufficient.

Host cells can prepare the polypeptides of the present invention which can be of a variety of chemical compositions. The polypeptide may be produced having methionine as its first amino acid. This methionine is present by virtue of the ATG start codon naturally existing at the origin of the structural gene or by being engineered before a segment of the structural gene. The protein may also be intracellularly or extracellularly cleaved, giving rise to the amino acid which is found naturally at the amino terminus of the polypeptide. The polypeptide may be produced together with either its own or a heterologous signal peptide, the signal polypeptide being specifically cleavable in an intra- or extracellular environment. Finally, the polypeptides of the present invention may be produced by direct expression in mature form without the necessity of cleaving away any extraneous polypeptide.

Recombinant host cells refer to cells which have been transformed with vectors constructed using recombinant DNA techniques. As defined herein, the polypeptides of the present invention is produced as a consequence of this transformation. The polypeptides of the present invention or fragments thereof produced by such cells are referred to as "recombinant polypeptides of the present invention."

Several groups of workers have isolated mixtures of messenger RNA (mRNA) from eukaryotic cells and employed a series of enzymatic reactions to synthesize double-stranded DNA copies which are complementary to this mRNA mixture. In the first reaction, mRNA is transcribed into a single-stranded complementary DNA (cDNA) by an RNA-directed DNA polymerase, also called reverse transcriptase. Reverse transcriptase synthesizes DNA in the 5'-3' direction, utilizes deoxyribonucleoside 5'-triphosphates as precursors, and requires both a template and a primer strand, the latter of which must have a free 3'-hydroxyl terminus. Reverse transcriptase products, whether partial or complete copies of the mRNA template, often possess short, partially double-stranded hairpins ("loops") at their 3' termini. In the second reaction, these "hairpin loops" can be exploited as primers for DNA polymerases. Preformed DNA is required both as a template and as a primer in the action of DNA polymerase. The DNA polymerase requires the presence of a DNA strand having a free 3'-hydroxyl group, to which new nucleotides are added to extend the chain in the 5'-3' direction. The products of such sequential reverse transcriptase and DNA polymerase reactions still possess a loop at one end. The apex of the loop or "fold-point" of the double-stranded DNA, which has thus been created, is substantially a single-strand segment. In the third reaction, this single-strand segment is cleaved with the single-strand specific nuclease S1 to generate a "blunt-end" duplex DNA segment. This general method is applicable to any mRNA mixture, and is described by Buell, et al., *J. Biol. Chem.*, 253:2483 (1978).

The resulting double-stranded cDNA mixture (ds-cDNA) is inserted into cloning vehicles by any one of many known techniques, depending at least in part on the particular vehicle used.

In general, methods can be found in Maniatis, et al., supra, and *Methods In Enzymology*, Volumes 65 and 68 (1980); and 100 and 101 (1983). In general, the vector is linearized by at least one restriction endonuclease, which will produce at least two blunt or cohesive ends. The ds-cDNA is ligated with or joined into the vector insertion site.

Once the DNA segments are inserted, the cloning vehicle is used to transform a suitable host. These cloning vehicles usually impart an antibiotic resistance trait on the host. Such hosts are generally prokaryotic cells.

If prokaryotic cells or other cells which contain substantial cell wall material are employed, the most common method for transformation with the expression vector is calcium chloride pretreatment as described by Cohen, R. N., et al., *Proc. Nat'l. Acad. Sci. USA*, 69:2110 (1972). If cells without cell wall barriers are used as host cells, transfection is carried out by the calcium phosphate precipitation method described by Graham and Van der Eb, *Virology*, 52:456 (1973). Other methods for introducing DNA into cells such as electroporation, nuclear injection, viral infection or protoplast fusion may be successfully used. At this point, only a few of the transformed or transfected hosts contain the desired cDNA. The sum of all transformed or transfected hosts constitutes a gene "library". The overall ds-cDNA library created by this method provides a representative sample of the coding information present in the mRNA mixture used as the starting material.

Clones containing part or the entire cDNA for the the polypeptides of the present invention are identified with specific oligonucleotide probes deduced from a partial amino acid sequence determination of the polypeptides of the present invention. This method of identification requires that the non-degenerate oligonucleotide probe be designed such that it specifically hybridizes to the cDNA corresponding to the present invention. Clones containing cDNA sequences encoding the polypeptides of the present invention are isolated as follows.

Individual transformed or transfected cells are grown as colonies on a nitrocellulose filter paper. These colonies are lysed; the DNA released is bound tightly to the filter paper by heating. The filter paper is then incubated with a labeled oligonucleotide probe which is complementary to the structural gene of interest. The probe hybridizes with the cDNA for which it is complementary, and is identified by autoradiography. The corresponding clones are characterized in order to identify one or a combination of clones which contain all of the structural information for the desired protein.

Clones containing additional sequence may also be identified using as probe the cDNA insert isolated during the initial screening of the cDNA library. Nucleotide sequencing techniques are used to determine the sequence of amino acids encoded by the cDNA fragments.

The nucleic acid sequence coding for the protein of interest is isolated and reinserted into an expression vector. The expression vector brings the cloned gene under the regulatory control of specific prokaryotic or eukaryotic control elements which allow the efficient expression (transcription and translation) of the ds-cDNA. Thus, this general technique is only applicable to those proteins for which at least a portion of their amino acid or DNA sequence is known for which an oligonucleotide probe is available. See, generally, Maniatis, et al., supra.

More recently, methods have been developed to identify specific clones by probing bacterial colonies or phage plaques with antibodies specific for the encoded protein of interest. This method can only be used with "expression vector" cloning vehicles since elaboration of the protein product is required. The structural gene is inserted into the vector adjacent to regulatory gene sequences that control expression of of the protein. The cells are lysed, either by chemical methods or by a function supplied by the host cell or vector, and the protein is detected by a specific antibody and a detection system such as enzyme immunoassay. An example of this is the lambda $gt_{11}$ system described by Young and Davis, *Proc. Nat'l. Acad. Sci. USA*, 80:1194–1198 (1983) and Young and Davis, *Science*, 222:778 (1983).

By providing the DNA sequences, and recombinant DNA molecules, the present invention also provides probes and methods to identify cells containing or lacking these sequences, and means to administer these sequences to cells. This will enable the establishment of systems in which the recombinant protein is produced after transfection of an expression vector into appropriate host cells. Additionally, the present invention provides a means to inhibit the expression of the novel sequences by providing an antisense RNA sequence which, when administered to a cell, or when the DNA encoding said antisense RNA is administered to a cell, said DNA sequence will produce an antisense RNA which can bind to and therefore block the expression of the RNA encoding the novel polypeptides of the present invention. It will also be apparent to one of skill in the art from this disclosure that antibodies against any of the proteins of the present invention can be utilized to block the binding of ligands to the polypeptides and to target drugs or other agents (such as labels) to the cells expressing these polypeptides.

Monoclonal antibodies of the present invention may be prepared using the method of Mishell, B. B., et al., *Selected Methods In Cellular Immunology*, (W. H. Freeman, ed.) San Francisco (1980). The 17-mer synthetic peptide was used as the antigen for the production of these antibodies. Briefly, a synthetic 17-mer OPF peptide was used to immunize spleen cells of Balb/C mice. The immunized spleen cells were fused with FO myeloma cells. Fused cells containing spleen and myeloma cell characteristics were isolated by growth in HAT medium, a medium which kills both parental cells, but allows the fused products to survive and grow.

The anti-OPF antibodies are useful in the treatment of disease states caused by increased levels in the individual of OPF. These treatments include administration of anti-OPF monoclonal antibodies to individuals suffering from osteoporosis, malignant diseases which affect the skeleton such as myeloma and breast cancer, and chronic inflammatory diseases which cause localized bone loss such as rheumatoid arthritis and periodontal disease. These antibodies are also useful in assays for detecting or quantitating levels of OPF. These assays provide a clinical diagnosis and assessment of those diseases in which excess production of these factors occurs, and a method for monitoring treatment efficacy. Synthetic antagonists to OPF have the same beneficial therapeutic effect as neutralizing antibodies in those diseases with this overproduction of OPF. Neutralizing antibodies will inhibit the activity of the excessively produced OPF in these individuals.

The term "individual" is meant to include any animal, preferably a mammal, and most preferably a rodent, cat, dog, cow or human.

The techniques for detectably labelling the homogeneous OPF and the monoclonal antibodies thereto of the present invention with a radiolabel, an enzyme label, or a fluorescent label are well known to those of skill in the art. Reference can be made to Chard, *An Introduction To Radioimmunoassay And Related Techniques*, North-Holland Publishing Co., Amsterdam-NY-Oxford (1978), *The Enzyme-Linked Immunoadsorbent Assay (ELISA)* by Voller, A., et al., Dynatech Europe Borough House, Rue du Pre, Guernsey, Great Britain, and *Radioiodination Techniques, Review* 18, Amersham Corporation, by A. E. Bolton, all incorporated herein by reference. Preferably, the purified OPF is labelled with $^{125}I$ using the Bolton/Hunter reagent which involves succinylation of the free N-terminals and lysine. DNA probes may also be labeled with a detectable label. Commonly used detectable labels are radioactive labels including, but not limited to, $^{32}P$, $^{14}C$, $^{125}I$, $^{3}H$ and $^{35}S$. Biotin labeled nucleotides can be incorporated into DNA or RNA by nick translation, enzymatic, or chemical means. The biotinylated probes are detected after hybridization using avidin/streptavidin, fluorescent, enzymatic or colloidal gold conjugates.

Nucleic acids may also be labeled with other fluorescent compounds, with immunodetectable fluorescent derivatives or with biotin analogues. Nucleic acids may also be labeled by means of attaching a protein. Nucleic acids cross-linked to radioactive or fluorescent histone HI, enzymes (alkaline phosphatase and peroxidases), or single-stranded binding (ssB) protein may also be used.

OPF to which there has been added a detectable label, such as a radioactive label such as 125 I, a fluorescent label such as fluorescein or rhodamine, biotin for non-covalent linking, or an enzymatic label such as alkaline phosphatase, a linking group, such as SASD (sulfosuccinimidyl 2-(p-azidosalicylamido) ethyl-1,3'-dithiopropionate a protecting or blocking group useful for specific reactive side groups during further chemical reactions or diagnostic assays, such as the omega-amino group of lysine. This can achieved using acylation and can be de-blocked using HCl and dioxane or neat trifluoroacetic acid plus thioanisole. Tyrosine can be modified by converting to amino tyrosine with tetranitromethane and sodium hydrosulfide. Other derivatives may also be prepared from the functional groups which occur at side chains on the residues of the N- or C-terminal groups, by means known in the art.

Administration of the compounds useful in the method of present invention may be by parenteral, intravenous, intramuscular, subcutaneous, rectal or any other suitable means. The dosage administered may be dependent upon the age, weight, kind of concurrent treatment, if any, and nature of the pathological state being treated. The effective compound useful in the method of the present invention may be employed in such forms as capsules, liquid solutions, suspensions or elixirs for oral administration, or sterile liquid forms such as solutions or suspensions. Any inert carrier is preferably used, such as saline, or phosphate-buffered saline, or any such carrier in which the compounds used in the method of the present invention have suitable solubility properties for use in the method of the present invention.

As used herein the term "salts" refers to both salts of carboxy groups of the polypeptide or protein chain and to acid addition salts of amino groups of the polypeptide chain. Salts of the carboxy group may be formed with either inorganic or organic bases by means known in the art per se. Inorganic salts include, for example, sodium, calcium, ammonium, ferric or zinc salts, and the like. Salts with organic bases include those formed, for example, with amines such as triethanolamine, arginine, lysine, piperidine, caffeine, procaine and the like. Acid addition salts include, for example, salts with mineral acids such as, for example, hydrochloric acid or sulfuric acid, and salts with organic acids such as, for example, acetic acid or oxalic acid.

Both the salts and the derivatives encompassed by the invention include those which are therapeutically or diagnostically acceptable, i.e., those which do not destroy the biologic, immunogenic, or binding activity of OPF depending on the functional activity desired to be utilized.

The term "specific activity" refers to the activity of OPF in OPF assays described in this application and known in the art related to the amount of protein by weight in the sample. As specified in the current disclosure, the activity of OPF is measured according to the assay procedures set forth hereinbelow in Examples 1, 2, and 5. Specific activity is calculated as shown in Example 3.

Having now generally described the invention, a more complete understanding can be obtained by reference to the following specific examples. These examples are provided for the purpose of illustration only and are not intended to be limiting unless otherwise specified.

EXAMPLE 1

Assay of OPF in Conditioned Medium from MH-85 Cells

The origin of the MH-85 tumor cells has been reported (Yoneda et al, (1991) J. Clin. Invest. 87:977–985; J. Clin. Oncol. 9:468–477). MH-85 cells were established in culture after isolation from a human squamous cancer of the maxilla. Six days after these cells are plated with an initial inoculation of $5 \times 10^5$ cells/2 ml well, $26 \times 10^5$ cells are present. The doubling time is approximately 28 hrs.

A modification of mouse bone marrow cultures developed by Takahashi et al was used to assess OPF activity in MH-85 CM and fractionated samples(Takahashi et al (1988) Endocrinology 122:1373–1382). Four to 6-week old male ICR Swiss mice (Harlan Industries, Houston, Tex.) were killed by cervical dislocation and immersed briefly in 80% ethanol. The femora and tibiae were removed aseptically and dissected free of adherent tissues. The bone ends were removed with a scalpel and the marrow cavity was flushed through with αMEM using 27G needles. Marrow cells from 3 to 5 mice were collected, washed twice with αMEM and incubated for 2 h on tissue culture plates. Nonadherent cells were resuspended in αMEM supplemented with 10% FCS (Hyclone, Logan, Utah) and no antibiotics at a final density of $4 \times 10^6$ cells per ml. Half a ml of cell suspension/well was inoculated onto 24 well plates (Corning, Corning, N.Y.) and 1,25-dihydroxyvitamin $D_3$ ($1,25D_3$) (Hoffman-La Roche, Nutley, N.J.) was added to each well at a final concentration of $10^{-8}$M. Appropriate dilutions of MH-85 CM or column fractions (5–25%) were added to the wells. Cultures were maintained at 37° C. in a humidified atmosphere of 5% $CO_2$ in air. The cells were fed every 2 days with 0.3 ml of fresh αMEM with 10% FCS and $10^{-8}$M $1,25D_3$. After 6 days, the cultures were washed in PBS, fixed in 60% acetone in citrate buffer pH 5.4 for 60 seconds, air dried and stained for tartrate resistant acid phosphatase (TRAP) using a commercially available kit (Sigma Chemical Co., St. Louis, Mo.). Multinuclearity and TRAP are characteristic properties of osteoclasts. Thus, the osteoclastic nature of the cells is confirmed by these parameters. Stained cultures were examined under light microscopy at ×200 magnification. TRAP positive (red staining) multinucleated (3 or more nuclei) cells (TRAP(+)MNC) were easily distinguishable from other cells present. All TRAP(+)MNC in each well were counted by manually scanning across the entire well in a systematic fashion.

MH-85 cells were grown in α-minimal essential medium (αMEM) supplemented with 5% fetal calf serum (FCS, Hazleton, Lenexa, Kans.) and 1% penicillin-streptomycin solution (GIBCO, Grand Island, N.Y.). Serum-free culture supernatants of MH-85 (MH-85CM) were harvested from 48 h incubation of subconfluent MH-85 cultures. As a control, conditioned media (CM) was harvested from another human squamous cancer of the maxilla (OKK) which was not associated with leukocytosis, hypercalcemia and cachexia. MH-85 conditioned media contained an activity which stimulates the formation of multinucleated cells from mouse mononuclear bone marrow cells, which comprise mononuclear precursors of osteoclasts. MH-85 CM caused a marked increase in the formation of multinucleated osteoclasts in these cultures, as assessed by the presence of tartrate-resistant acid phosphatase (TRAP) and their capacity to form pits (resorption lacunae) on a bone substitute (sperm whale dentine). FIG. 1 demonstrates the effect of MH-85 CM on tartrate-resistant acid phosphatase in multinucleated cells TRAP(+)MNC formation in mouse bone marrow cultures. Serum-free MH-85 CM was harvested from 48 h incubation of sub-confluent cultures, centrifuged and assayed in mouse bone marrow cultures ($2 \times 10^6$ cells/0.5 ml/well, 24-well plates) in the presence or absence of $10^{-8}$M, 1,25-dihydroxyvitamin $D_3$ (1,25$D_3$). 1,25$D_3$ is added as a differentiation factor for this assay. After 6 days, cells were stained for TRAP activity and numbers of TRAP(+)MNC were counted. Each value represents the mean±S.E. of 4 wells. There was a statistically significantly increase in TRAP-positive multinucleated cells (cells with osteoclast characteristics) in the cultures in response to MH-85 CM, both in the presence and absence of 1,25$D_3$ ($p<0.01$ Student's T-test). One asterisk indicates that a value is significantly different from the control. Two asterisks indicates that a value is significantly different from cultures treated with 1,25$D_3$ or MH-85CM alone.

This stimulatory effect was dose-dependent and maximal at 20% of CM concentration. This effect was enhanced in the presence of $10^{-8}$M 1,25$D_3$. CM from another human tumor (OKK) which was not associated with increased osteoclastic bone resorption, hypercalcemia and leukocytosis had no effect.

EXAMPLE 2

Assay for Bone-Resorbing Activity of TRAP(+)MNC (Multinucleated Cells with Osteoclast Characteristics)

Quantitation of the effects of TRAP(+)MNC on calcified matrices (sperm whale dentine) was performed using minor modifications of the disaggregated osteoclast resorption assay, as described by Boyde et al (1984) Br Dent J 156:216. Mouse bone marrow cells, prepared as described above, were cultured in α-MEM supplemented with 10% FCS on slices of sperm whale dentine for 8 days in the presence of $10^{-8}$M 1,25$D_3$ and MH-85 CM or partially-purified factors. Slices of sperm whale dentine ($0.25 \times 10 \times 8$ mm) were prepared using a Buehler low speed diamond saw (Buehler, Lake Bluff, Ill.), followed by sonication (15 min) in several changes of distilled water. Slices were smoothed between 2 glass plates and sterilized under UV light for 4 days. Before all experiments, slices were incubated in αMEM supplemented with 10% FCS and 1% penicillin-streptomycin solution (GIBCO) for at least 48 h. Cultures were performed in 24-well microtiter plates in humidified air (10% $CO_2$) at 37° C. (1 slice/well). A single experiment used 16–20 slices, with a minimum of 3–4 slices/treatment. After 8-days of culture, some of the slices with cells stained for TRAP and TRAP(+)MNC were examined under light microscopy. For examination of resorption lacunae (pits), the slices were sonicated in 0.1M NaOH and stained with 0.1% (IV/V) toluidine blue. Lacunae were examined using light microscopy, and the plan area of matrix resorbed was quantitated using a computer-assisted morphometric program on a Quantex image and process analysis system (Quantex Instruments, Sunnybrook, Calif.). Data were analyzed by pattern analysis of variance (Oreffo et al, (1990) Endocrinology 126:3069–3075).

EXAMPLE 3

Purification of OPF

One hundred liters of serum-free MH-85 CM was collected, concentrated by ultrafiltration using a Pellicon cassette (Millipore, Bedford, Mass.) with a filter of nominal molecular weight cut-off of 10,000 to 2.5 liter and precipitated with 80% (W/V) ammonium sulfate. The precipitate was dissolved in 180 ml distilled water and dialyzed against distilled water [16 liters for about 24 hours] and then against 10 mM sodium phosphate buffer (pH 8.3)[3 changes of 16 liters for about 24 hours per change].

The concentrated and dialyzed MH-85 CM was fractionated by anion exchange chromatography on a $4.8 \times 30$ cm DEAE-Cellulose DE-52 (Whatman, Hillsboro, Oreg.) column equilibrated with 10 mM phosphate buffer (pH 8.3) at a flow rate of 90 ml/h using a step-wise gradient of sodium phosphate buffer. Twenty ml fractions were collected and aliquots (1 ml) were tested for TRAP(+)MNC formation as described in Example 1. There were 2 peaks of activity which stimulated TRAP(+)MNC formation in the mouse bone marrow culture assay. This activity was shown to be effected by OPF. The 2nd peak, which eluted at a different position from other known colony stimulating factors, such as GM-CSF, G-CSF and M-CSF, eluted between 0.04 and 0.06M phosphate (FIG. 2). FIG. 2 demonstrates the profile of the DEAE-Cellulose anion exchange column chromatography. Aliquots (2 ml) were taken from each fraction (20 ml/fraction), dialyzed, lyophilized, reconstituted in culture medium and assessed for their OPF activity in mouse marrow culture assay in the presence of $10^{-8}$M 1,25$D_3$ and CSF activity in human marrow culture colony forming assay. The total activity of the polypeptide was determined by counting the number of TRAP(+) multinucleated cells at the end of the culture period and multiplying the total number of positive cells by $10^4$ (since 0.01% of 100 l total starting sample was assayed). Specific activity was calculated as total activity divided by amount of protein in mg multiplied by $10^{-3}$. Table 2 demonstrates that at least a 4519 fold purification was obtained following DEAE chromatography.

TABLE 2

| | Purification of OPF | | | | |
| Purification Step | Total Protein (mg) | Total Activity Cells × 10$^{-4}$ | Specific Activity | Fold-Purification | Recovery % |
| --- | --- | --- | --- | --- | --- |
| Serum-free MH-85CM | 1820 | 170 | 0.9 | 1 | 100 |
| Concentration 10kD cut off membrane | 1526 | 161 | 1.1 | 1 | 95 |
| 80% $(NH_4)_2SO_4$ Precipitation | 1247 | 139 | 1.1 | 1 | 82 |
| DE-52 Column | 0.3 | 122 | 4067 | 4519 | 72 |

TABLE 2-continued

| | Purification of OPF | | | | |
|---|---|---|---|---|---|
| Purification Step | Total Protein (mg) | Total Activity Cells × 10$^{-4}$ | Specific Activity | Fold- Purification | Recovery % |
| Gel Filtration Sephadex 6-50 | 0.01 | 34 | 34,000 | 37800 | 20 |
| RP HPLC | 0.003 | 33 | 110,000 | 122,200 | 19 |

Figure 3:
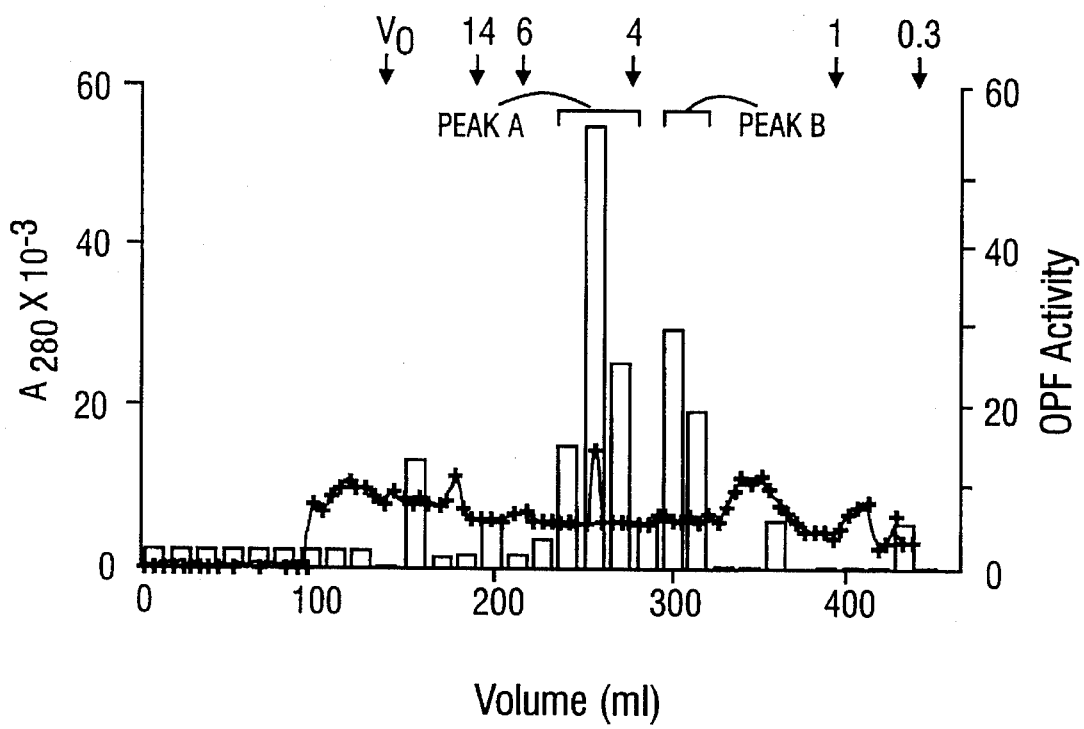
FIG. 3 demonstrates the profile of Sephadex-G50 gel filtration chromatography of Peak 2 from DEAE-Cellulose column.

The pooled fractions of peak 2 were further purified using gel filtration chromatography. The active fractions obtained from DEAE-Cellulose chromatography were pooled, dialyzed overnight against 50 mM ammonium bicarbonate (pH 7.2) and lyophilized. (Approximately 200 mls of pooled fractions were dialyzed against 4 changes of 16 liters of dialysis buffer). The lyophilized material was dissolved in approximately 0.5 ml of 50 mM ammonium bicarbonate and fractionated by size exclusion chromatography on a 2.5×60 cm Sephadex G-50 column. (Pharmacia, Piscataway, N.J.) column equilibrated with 50 mM ammonium bicarbonate at a flow rate of 30 ml/h. A broad peak of activity which stimulated the formation of TRAP(+)MNC was eluted at positions of molecular weight of about 4 kD on a Sephadex G-50 column (FIG. 3). FIG. 3 demonstrates the profile of Sephadex-G50 gel filtration chromatography of Peak 2 from DEAE-Cellulose column. Aliquots (1 ml) were taken from each fraction (10 ml/fraction), lyophilized, reconstituted in αMEM supplemented with 10% FCS and assayed for their OPF activity in mouse marrow culture assay in the presence of $10^{-8}$M 1,25D$_3$.

Standard molecular weight marker proteins used were blue dextran (void volume), ribonuclease (14K), insulin (6K), a peptide synthesized in our laboratory of 1 k, and phenol red (0.3K).

When mouse bone marrow cells were cultured on sperm whale dentine in the presence of $10^{-8}$M 1,25D$_3$ and with or without the active peak from Sephadex-G50 chromatography, characteristic resorption pits were found. In the presence of this peak, much greater numbers of TRAP(+)MNC and increased area of resorption lacunae (pits) were seen. These findings demonstrated that the active peak contained a biological activity which increases the formation of mouse multinucleated cells with osteoclast characteristics in long-term marrow cultures.

Figure 4:
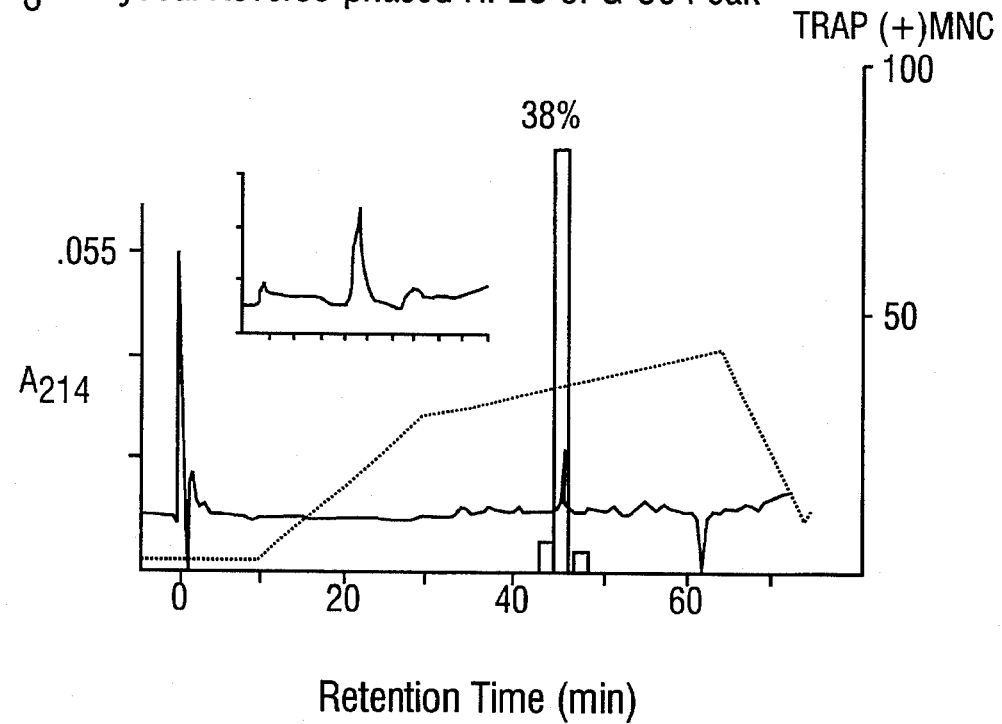
FIG. 4 demonstrates the profile of C8 RP HPLC column.

This first part of this active peak (peak A from FIG. 3) was further chromatographed on a C8 reverse phase HPLC analytical column (2.1×150 mm) with a gradient of 0.1% TFA and 0.1% TFA/70% acetonitrile at a flow rate of 0.15 ml/min. The absorbance was monitored at 214 nm. FIG. 4 demonstrates the elution profile of C8 RP HPLC column. To measure the biological activity in HPLC fractions, an aliquot of 5% of each fraction was lyophilized in the presence of carrier BSA and reconstituted in cell culture media. Activity was then assayed on marrow mononuclear cell cultures. The biologically active fraction containing osteoclastpoietic activity eluted from this column at 38% acetonitrile (45 min).

The final product had a specific activity of 110,000 demonstrating a total purification greater than 120,000 fold.

EXAMPLE 4

Synthesis of Biologically Active OPF polypeptide (17-mer)

The fraction from the HPLC purification of Example 3 containing the biological activity was digested with Lys-C according to the method of (Matsudaira P: Limited N-terminal sequence analysis. In Guide to Protein Purification (ed. Deutscher MP), Methods in Enzymology, Vol. 182, Academic Press, Inc., San Diego, pp. 602–612, 1990.). Resulting peptide fragments were isolated by reverse phase microbore HPLC under the same conditions as described in Example 3. The amino acid sequence of one of the fragments was established using a pulsed-liquid gas-phase microsequencer (Applied Biosystems gas-phase microsequencer).

A novel peptide of 18 amino acids was obtained following enzyme digestion. The amino acid sequence was - K-A-V-Q-R-Y-L-V-L-Q-G-V-S-P-A-Q-L, (SEQ ID NO: 2). The first amino acid (K) is assumed, based on knowledge of the enzymatic properties of Lys-C.

Figure 5A:
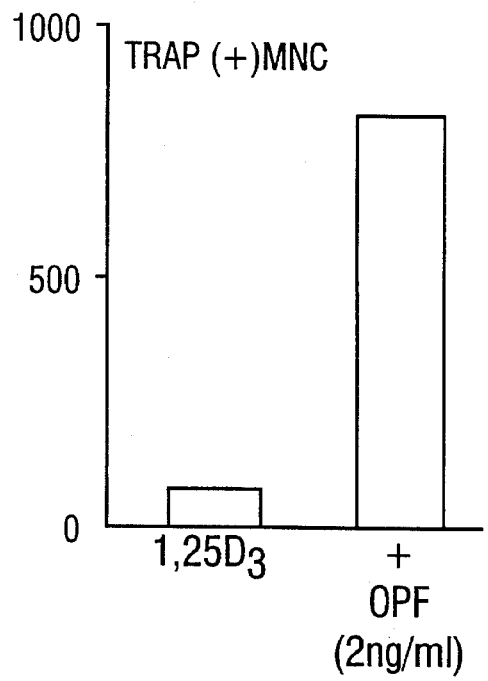
FIGS. 5A–5B demonstrate the effects of synthetic peptide on mouse bone marrow cultures; effects on formation of TRAP(+) multinucleated cells (FIG. 5A), effects on capacity to form resorption pits (FIG. 5B).
Figure 5B:
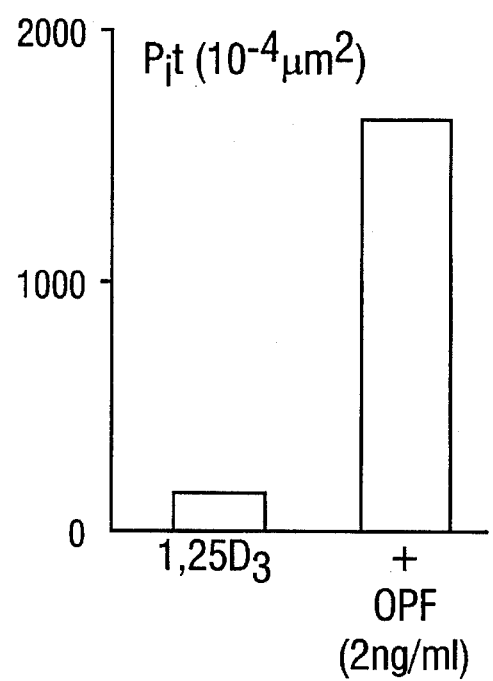

A 17-mer synthetic peptide was prepared having the same amino acid sequence, using an Applied Biosystems 480A peptide synthesizer. When the activity of the synthetic peptide was tested in mouse bone marrow cultures, it produced identical effects to those seen with MH-85 conditioned media or partially purified OPF fractions. FIG. 5 demonstrates that 2 ng/ml of the synthetic peptide increased the formation of multinucleated cells which were TRAP positive (panel 5a), and formed resorption lacunae (panel 5b). This peptide was active in concentrations of 0.01–2 ng/ml.

EXAMPLE 5

Effects of the Synthetic Peptide

Figure 6:
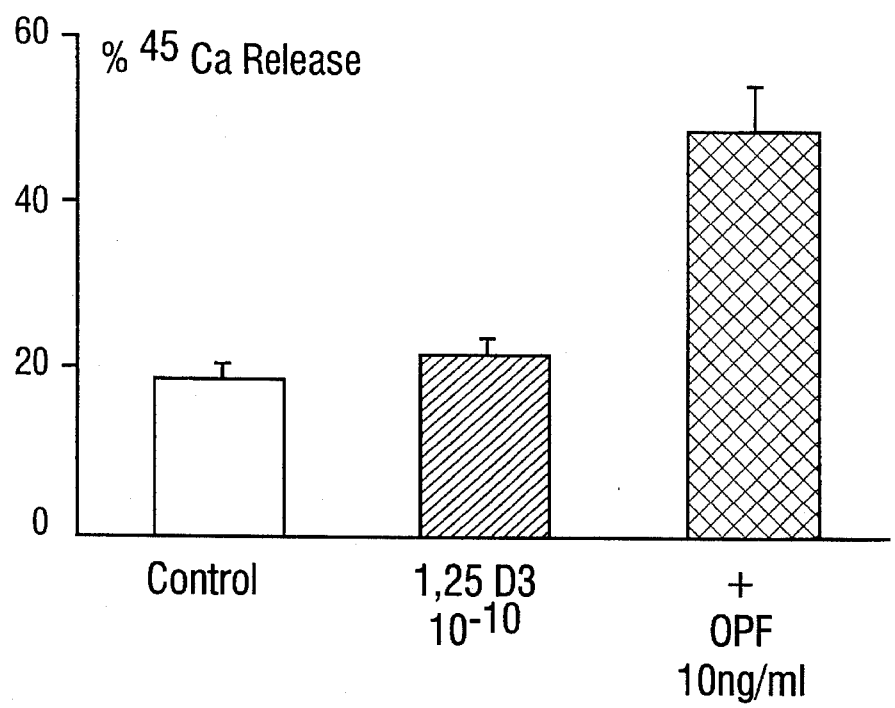
FIG. 6 demonstrates the effects of a synthetic peptide on bone resorption in organ cultures of fetal rat long bones.
Figure 7:
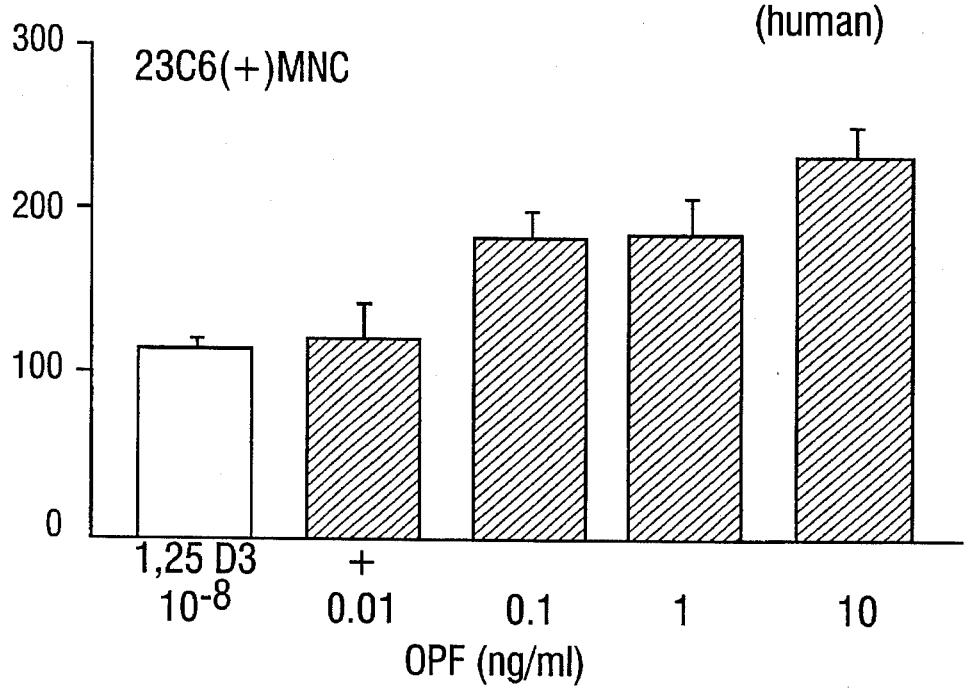
FIG. 7 demonstrates the effects of a synthetic peptide on human marrow cultures.

The synthetic peptide was tested in the same assays as the original conditioned media. It was initially tested on the formation of multinucleated cells with osteoclast characteristics (staining with tartrate-resistant acid phosphatase) in murine marrow cultures. At concentrations of 2 ng/ml, the synthetic peptide caused a profound increase in the formation of TRAP-positive multinucleated cells. In addition, the effects of the synthetic peptide were tested for the capacity to stimulate murine marrow cultures to form multinucleated cells which have the capacity to form resorption pits on calcified matrix (sperm whale dentine). FIG. 6 demonstrates the effect of the synthetic 17-mer OPF peptide (10 ng/ml) on bone resorption as assessed by $^{45}$Ca release from fetal rat long bones in organ culture. There was a similar increase in the number and area of resorption pits as that seen when murine marrow cultures were cultured with the conditioned media from MH-85 cultures. The peptide was also tested in other bone resorption assays, including the capacity to stimulate the formation of cells with osteoclast characteristics from human bone marrow cultures and its capacity to stimulate bone resorption in organ cultures of fetal rat long bones. It was effective in both of these assays in concentrations between 2–10 ng/ml. FIG. 7 demonstrates the effects of the 17-mer synthetic OPF peptide on human osteoclast cell formation at doses ranging from about 0.01 to about 10 ng/ml. Maximal activity was observed at about 2 ng/ml.

EXAMPLE 6

Purification of OPF Polyclonal Antibodies Using Affinity Chromatography

The synthetic peptide was synthesized using F-MOC chemistry. Half of it had cysteine added to the N-terminal end. The amino terminus was coupled through the sulfhydryl group to an affinity column. Once this affinity column was made, 80 mls of rabbit serum containing polyclonal antibody to OPF was ammonium sulphate precipitated, dialyzed, and subjected to the peptide affinity column. It was eluted with 0.2M glycine (pH 2.8) and approximately 3 mg of purified antibody was retrieved.

EXAMPLE 7

Preparation of Polyclonal antibodies to OPF

Rabbits (male, 6 to 8 week-old) were subcutaneously injected (10 sites/animal, 100 µl/site) with 1.3 mg keyhole lympet hemocyanin (KLH)-conjugated synthetic 17-mer peptide and 2 ml complete Freund's adjuvant. Four weeks after the first immunization, animals were boosted intramuscularly with 1.3 mg KLH-conjugated synthetic 17-mer peptide and 2 ml incomplete Freund's adjuvant 3 times. At each booster, blood was drawn from an ear vein and tested for its titer against the synthetic 17-mer peptide by ELISA.

EXAMPLE 8

Affinity Purification of OPF

An alternative method for purification of OPF is to utilize polyclonal or monoclonal antibodies for affinity purification. Polyclonal or monoclonal antibodies were used in an affinity column to absorb biological activity from MH-85 CM, which was eluted from the affinity column with 4 mls of 1M acetic acid. The eluted fractions are highly enriched in OPF and can be chromatographed on a reverse-phase high performance liquid chromatography column to assess the purity.

The purified antibody prepared as in Example 7 was coupled through the amine group to a second affinity matrix. The binding capacity of the 17-mer affinity column was greater than 3 µg. The antibody was eluted from the column with 0.2M glycine at low pH (pH 2.8). Next, 500 ml of MH-85 CM was processed through this antibody affinity column and no activity was present in the flow-through fraction. The bound fraction was eluted with two types of elution buffer, 0.1–0.2M glycine and 1M acetic acid. ELISA assay of the eluates demonstrated that 1M acetic acid was more effective at eluting the immunoreactive material than the 0.2M glycine. Therefore, acetic acid is a preferred eluting buffer.

EXAMPLE 9

Preparation of Monoclonal Antibodies to OPF

Figure 8:
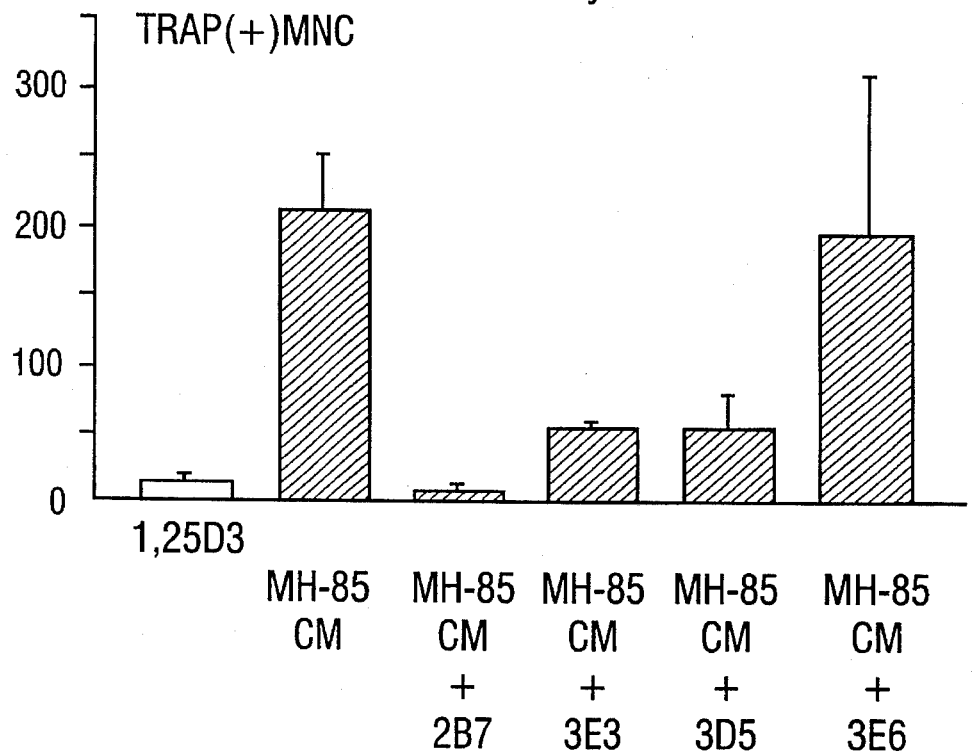
FIG. 8 demonstrates the effects of different monoclonal antibodies raised against the synthetic peptide (17-mer) on biological activity due to OPF in MH-85 conditioned medium.

Monoclonal antibodies (MAb) to OPF were made using an in vitro immunization technique (Van Ness et al, (1983) Nature 301: 425–427. Spleen cells of 8 to 12 week-old female Balb/C mice were immunized with 250 pg synthetic 17-mer peptide in the presence of 100 µg N-acetylmuramyl-L-alanyl-D-isoglutamine (MDP, Sigma), 125 µg lipopolysaccharide (LPS, Difco) and 500 µl culture supernatants of concanavalin A (50 µg/ml)-stimulated spleen cells ($5 \times 10^6$/ml) in 5 ml IMDM supplemented with 20% FBS in 6-well plates for 4 days. The immunized spleen cells were then hybridized with mouse myeloma FO cells (kindly provided by Dr. Eguchi, Kaneka, Japan) at a ratio of 2:1 in the presence of 50% polyethylene glycol (1500, Boehringer-Manheim). After the hybridization, the cells were suspended in 120 ml IMDM supplemented with 10% FBS and 0.5 ml cell suspension were inoculated onto each well in 48-well plates. After 24 hours, $5 \times 10^5$/well thymocytes in 0.5 ml HAT medium were plated onto each well as a feeder layer. The plates were cultured for 14 days in HAT medium (Flow) and then for 7 to 10 days in HT medium (Flow). The cells were fed fresh medium every 2 days. The culture supernatants harvested from the wells in which growing hybridoma cells cover 50% of the surface area were screened for their cross reactivity with the synthetic 17-mer peptide by enzyme-linked immunosorbent assay (ELISA). FIG. 8 demonstrates that at least 3 of the monoclonal antibodies neutralized (inhibited) the biological activity of OPF. Medium from hybridoma cells producing monoclonal antibodies designated 2B7, 3E3, 3D5 and 3E6 was diluted 1:10 in TRAP incubation buffer and incubated with an equal volume of 10% MH-85 CM. As demonstrated on FIG. 8, antibodies designated 2B7, 3E3, 3D5 neutralized the OPF activity in MH-85 CM. Since these antibodies were derived to the synthetic peptide, this data further comfirms that the amino acid sequence in the synthetic peptide confers the biological activity present in MH-85 CM.

EXAMPLE 10

Enzyme-linked immunosorbent assay (ELISA) for OPF

The ELISA plates (Nunc) were coated with 100 ng/50 µl/well synthetic 17-mer peptide overnight at 4° C., washed with 200 µl/well phosphate-buffered saline (PBS) twice, incubated with 200 µl/well blocking buffer (1% bovine serum albumin in PBS) for 1 hour at 37° C. and rinsed with 250 µl washing buffer (0.05% Tween 20 in PBS). The plates were then incubated with 200 µl/well hybridoma culture supernatants to be tested for overnight at 4° C. and rinsed with 250 µl/well washing buffer 3 times. After rinsing, the plates were incubated with 200 µl/well peroxidase-conjugated goat anti-mouse immunoglobulin G antibodies for 1 hour at 37° C., rinsed with 250 µl/well washing buffer 5 times and incubated with 200 µl/well 0-phenylenediamine dihydrochloride (OPD) solution (4 mg OPD and 10 µl 30% hydrogen peroxide in 10 ml water) for 10 to 20 minutes. The reaction was stopped by adding 80 µl/well 2.5M sulfuric acid. The absorbance was read at 492 nm. The limits of detection in this assay are 50 pg/ml.

DEPOSIT OF STRAINS USEFUL IN PRACTICING THE INVENTION

Deposits of biologically pure cultures of the following strains were made under the Budapest Treaty with the American Type Culture Collection, 12301 Parklawn Drive, Rockville, Md., The accession numbers indicated were assigned after successful viability testing, and the requisite fees were paid.

Access to said cultures will be available during pendency of the patent application to one determined by the Commissioner of the United States Patent and Trademark Office to be entitled thereto under 37 C.F.R. §1.14 and 35 U.S.C. §122, or if and when such access is required by the Budapest Treaty. All restriction on availability of said cultures to the public will be irrevocably removed upon the granting of a patent based upon the application and said cultures will remain permanently available for a term of at least five years after the most recent request for the furnishing of samples and in any case for a period of at least 30 years after the date of the deposits. Should the cultures become nonviable or be inadvertently destroyed, they will be replaced with viable cultures(s) of the same taxonomic description.

| Strain/Plasmid | ATCC No. | Deposit Date |
|---|---|---|
| MH-85 | CRL 10833 | July 23, 1991 |
| OPF3E3 | HB10534 | July 23, 1991 |

One skilled in the art will readily appreciate the present invention is well adapted to carry out the objects and obtain the ends and advantages mentioned, as well as those inherent therein. The peptides, antibodies, methods, procedures and techniques described herein are presented as representative of the preferred embodiments, or intended to be exemplary and not intended as limitations on the scope of the present invention. Changes therein and other uses will occur to those of skill in the art which are encompassed within the spirit of the invention or defined by the scope of the appended claims.

What is claimed as new and intended to be covered by Letters Patent of the United States is:

1. An isolated and purified biologically active polypeptide capable of stimulating the growth or differentiation of osteoclast cells comprising the amino acid sequence -A-V-Q-R-Y-L-V-L-Q-G-V-S-P-A-Q-L (SEQ ID NO: 1).

2. A biologically active polypeptide according to claim 1, having a molecular weight of from 1000 daltons to 6000 daltons as determined by gel filtration chromatography.

3. A polypeptide according to claim 2, modified to be in detectably labeled form.

4. An isolated and purified antibody capable of specifically binding to the polypeptide of claim 1.

5. An antibody capable of specifically binding to the polypeptide according to claim 1, wherein said polypeptide is isolated from the human squamous tumor cell line MH-85, which has been deposited as ATCC number HB 10833.

6. The antibody of claim 4 which is a monoclonal antibody.

7. The antiody of claim 4 which is a polyclonal antibody.

8. A hybridoma cell line which produces the monoclonal antibody of claim 6.

9. The hybridoma cell line of claim 8 which has been deposited as ATCC number HB 10834.

10. The polypeptide according to claim 1 purified by immunoaffinity chromatography from the squamous tumor cell line MH-85, which has been deposited as ATCC number HB 10833.

11. An isolated and purified antibody capable of neutralizing the biological activity of the polypeptide of claim 1.

12. The antibody of claim 11 which is a monoclonal antibody.

13. The antibody of claim 11 which is a polyclonal antibody.

14. A biologically active polypeptide according to claim 1 having a specific activity of at least 1 Unit per mg of protein, where Units are defined as the number of tartrate-resistant acid phosphatase positive multinucleated cells in the mouse marrow culture assay multiplied by $10^{-3}$.

15. A biologically active polypeptide according to claim 1 having a specific activity of at least 4067 Units per mg of protein, where Units are defined as the number of tartrate-resistant acid phosphatase positive multinucleated cells in the mouse marrow culture assay multiplied by $10^{-3}$.

16. A biologically active polypeptide according to claim 1 having a specific activity of at least 110,000 Units per mg of protein, where Units are defined as the number of tartrate-resistant acid phosphatase positive multinucleated cells in the mouse marrow culture assay multiplied by $10^{-3}$.

17. A hybridoma cell line which produces the monoclonal antibody of claim 12.

18. The monoclonal antibody produced by the hybridoma cell line of claim 9.

* * * * *